United States Patent [19]

Tanimoto et al.

[11] Patent Number: 5,075,424

[45] Date of Patent: Dec. 24, 1991

[54] PROCESS FOR PRODUCING KAPPA-CASEIN GLYCOMACROPEPTIDES

[76] Inventors: Morimasa Tanimoto, 101, Howaito Paresu, 470-7, Mizuno, Sayama-shi, Saitama-ken; Yoshihiro Kawasaki, Yukijirushi Nyugyo Kabushikikaisha Dokushin-ryo, 11-3, Arajukucho 5-chome, Kawagoe-shi, Saitama-ken; Hiroshi Shinmoto, 109, Sanraizu Haitsu, 3-61, Asahicho 1-chome, Kawagoe-shi, Saitama-ken; Shunichi Dosako, #616, 15-39, Kitaurawa 5-chome, Urawa-shi, Saitama-ken; Akira Tomizawa, 30-502, Shinsayama Haitsu, 63, Aoyagi, Sayama-shi, Saitama-ken, all of Japan

[21] Appl. No.: 476,196

[22] Filed: Feb. 7, 1990

[30] Foreign Application Priority Data

Apr. 19, 1989 [JP] Japan .................................. 1-97583

[51] Int. Cl.$^5$ .............................................. C07K 15/14

[52] U.S. Cl. ................................... 530/361; 530/322; 530/360; 530/395

[58] Field of Search ............... 530/322, 360, 832, 833, 530/361, 395

[56] References Cited

FOREIGN PATENT DOCUMENTS 0283675 9/1988 European Pat. Off. .
0291264 11/1988 European Pat. Off. .
0291265 11/1988 European Pat. Off. .

*Primary Examiner*—Howard E. Schain

[57] ABSTRACT

A process for producing κ-casein glycomacropeptides which comprises adjusting the pH of a solution of milk starting materials containing the κ-casein glycomacropeptides to below 4, treating the solution by ultrafiltration with a membrane having a fraction molecular weight of 10,000–50,000, and concentrating the obtained filtrate with a membrane having a fraction molecular weight of 50,000 or less.

8 Claims, No Drawings

PROCESS FOR PRODUCING KAPPA-CASEIN GLYCOMACROPEPTIDES

BACKGROUND OF THE INVENTION

The present invention relates to a process for the simple production of κ-casein glycomacropeptides which have several useful physiological activities.

It is known that κ-casein glycomacropeptides are peptides bonded with sialic acid which are produced by reacting milk κ-casein with rennet or pepsin and are present in cheese whey.

Hitherto, κ-casein glycomacropeptides were produced by a method comprising dissolving κ-casein isolated from cow's milk in deionized water, reacting the obtained solution with pepsin, adding trichloroacetic acid to the solution to precipitate a para-κ-casein fraction, dialyzing the obtained supernatant against deionized water for desalting, and freeze-drying the obtained solution (Bulletin of Experimental Biology and Medicine, 96, 889 (1983)). Another method comprised dissolving the above κ-casein in deionized water, adjusting the pH of the solution to 6.7, reacting the solution with rennet, readjusting the pH to 4.6 to precipitate the para-κ-casein, removing the precipitate, dialyzing the obtained supernatant for desalting, and freeze-drying the obtained solution (Milk Protein, Academic Press Company, pp 200).

However, these methods are conducted in laboratories and are not suitable for mass production.

On the other hand, since the industrial utilization of κ-casein glycomacropeptides has been previously unknown, a method for producing such compounds in large quantities has not been studied.

Since it was reported that after taking κ-casein glycomacropeptides dogs lost their appetite (Bulletin of Experimental Biology and Medicine, 96, 889 (1983)), it has been found that the compounds can be utilized as food materials for the prevention of fat.

Further, since it was found that κ-casein glycomacropeptides were effective to prevent the adhesion of E.coli to cells of the intestines, to protect the infection of influenza (Japanese Unexamined Patent Application No. 63-284133/1988) or to protect the adhesion of tartar to teeth (Japanese Unexamined Patent Application No. 63-233911/1988), the demand for the production of these compounds on a large industrial scale is expected.

Given such conditions, a process for preparing a κ-casein glycomacropeptide from rennet casein curd whey has been reported. (Japanese Unexamined Paten Application No. 63-284199). Since the reaction of the process may proceed without the trichloroacetic acid of the prior art; the obtained compounds can be used as food materials and can be produced in a large quantity. However, the method can not be used with the rennet casein curds which are obtained as a by-product of the rennet casein curd whey.

If the rennet casein curds are not utilized, the production cost of κ-casein glycomacropeptides is expensive.

SUMMARY OF THE INVENTION

The present inventors have found that the molecular weight of the κ-casein glycomacropeptides changes sharply at pH 4.

Accordingly, an object of the present invention is to provide a simplified process for the production of κ-casein glycomacropeptides at a low cost utilizing the above mentioned change of the molecular weight at pH 4.

The present invention provides a process for producing a κ-casein glycomacropeptide, characterized in that the process comprises adjusting the pH to below 4 of a solution of milk starting materials such as cheese whey, whey protein concentrate and cheese whey from which protein has been removed, treating the solution by ultrafiltration with a membrane having a fraction molecular weight of 10,000–50,000 to obtain the filtrate of the solution, preferably readjusting the pH of the filtrate to 4 or higher, and concentrating the obtained filtrate with a membrane having a fraction molecular weight of 50,000 or less to obtain the desalted concentrate.

DETAILED DESCRIPTION OF THE INVENTION

It is known that the κ-casein glycomacropeptides are liberated from casein in the production of cheese. The following may be used as raw materials in the present invention cheese whey: whey protein concentrate which is produced by either ultrafiltration, ion-exchange chromatography or gel filtration; cheese whey from which a whey protein precipitate has been removed by heat treatment; or lactose mother liquor. When the whey protein concentrate is used, it is diluted with water to obtain a preferred concentration of 20% or less by weight. If the concentration is too high, the flow rate of the ultrafiltration is decreased. Any kind of cheese whey can be used. Since small quantities of casein curds and fatty contents remain in the cheese whey, they are removed with a centrifuge, a cream separator or a clarifier prior to use. Lactose principally contained in the cheese whey from which protein has been removed by heating, is precipitated by the treatment. The precipitated lactose is removed with a centrifuge, a clarifier or by decantation, and the cheese whey is warmed.

Then, the pH value of the whey is adjusted to 4 or lower, preferably to 3.5±0.2. When the pH value is 4 or higher, the molecules of the κ-casein glycomacropeptide are associated, the molecular weight becomes greater and these molecules are difficult to pass through the membrane. The lower limit of the pH value is not particularly limited. When the pH value is 3 or lower, sialic acid which is bonded to the κ-casein glycomacropeptide becomes unstable, so that the physiological effectiveness of the compound is lowered. However, when a κ-casein glycomacropeptide having no sialic acid is required, the pH value may be 3 or lower. The pH adjustment can be achieved using an acid. For such an acid, hydrochloric acid, sulfuric acid, acetic acid, lactic acid, citric acid, etc. may be exemplified.

After adjusting the pH value, the solution is ultrafiltered. The fraction molecular weight of the membrane used in the ultrafiltration stage is 10,000 to 50,000. When a membrane having the fraction molecular weight below 10,000 is used, the molecules of the κ-casein glycomacropeptide are difficult to pass through the membrane. When a membrane having the fraction molecular weight above 50,000 is used, the molecules of the κ-casein glycomacropeptide can pass through the membrane and a part of the coexisting whey protein can also pass through the membrane, so that the purity of the κ-casein glycomacropeptide is decreased. Usually, in the production process of whey protein concentrate, the whey protein is ultrafiltered with a module equipped with a membrane having a fraction molecular weight of about 20,000. In the process of the present invention, the above membrane can be used.

In the ultrafiltration stage, the solution is preferably concentrated up to the limit and thus an improved yield rate of the filtrate is achieved.

It is also preferred that water is added to the concentrated solution and the ultrafiltration is conducted, repeatedly. For increasing the flow rate of the filtrate, the solution may be heated at about 50° C. However, when the temperature is above 60° C., the whey protein is precipitated or gels, so that the solution is preferably heated at 60° C. or less. The obtained concentrate is dried after adjusting the pH value to neutral to obtain the powder of whey protein concentrate.

The filtrate obtained by a such process contains the κ-casein glycomacropeptide, lactose and mineral. Since the concentration of the κ-casein glycomacropeptide is lowered, the filtrate should be desalted and concentrated, The two methods of desalting and concentrating are as follows.

In the first method, after readjusting the pH of the filtrate to 4 or higher, the filtrate is filtered with a membrane having the fraction molecular weight of 50,000 or less by ultrafiltration, diafiltration or reverse osmosis hyperfiltration. The pH of the filtrate can be adjusted by an alkali such as, for example sodium hydroxide, sodium bicarbonate or ammonia. The monomer of the κ-casein glycomacropeptide (molecular weight 9,000) is obtained at the pH value of 4 or lower, and the polymer of κ-casein glycomacropeptide (molecular weight 45,000) is obtained at the pH value above 4. If desired, the pH value is adjusted to 5 or higher. Further, any membrane having the fraction molecular weight 50,000 or less can be used in the process of the present invention. When the membrane has the fraction molecular weight above 50,000, the κ-casein glycomacropeptide can pass through the membrane. A membrane having the molecular weight about 20,000 which is used in the usual process of producing the concentrate of whey protein can be conveniently used.

When the pH of the filtrate is not readjusted to 4 or higher, the κ-casein glycomacropeptide exists in the monomer, form. Then, the second method is used. In the method, the concentrate is obtained by means of a membrane having the fraction molecular weight of 10,000 or less, preferably 8,000 or less by ultrafiltration, diafiltration or reverse osmosis hyperfiltration.

These methods can be combined with a desalting process, e.g. by means of electrodialysis or by using an ion exchange resin.

Since the obtained concentrate substantially contains only the κ-casein glycomacropeptide, it can be dried by spray drying or freeze-drying. Furthermore, since the κ-casein glycomacropeptide is stable to heat, it is preferred to add a pasteurizing or a sterilizing step prior to the drying step.

As described above, according to the present invention, the pH value of the solution of milk starting materials such as cheese whey, whey protein concentrate and cheese whey from which protein has been removed is adjusted. Such a simple operation can provide a process of producing κ-casein glycomacropeptides on a large scale and at a low cost. The obtained product has high purity.

Moreover, in a factory where the whey protein concentrate has been produced, new equipment is not required because κ-casein glycomacropeptides can be produced with the ultrafilter or the reverse osmosis hyperfilter for preparing the whey protein concentrate. The protein fraction from which the κ-casein glycomacropeptides has been removed can be used as the whey protein concentrate.

Further, the products can be obtained without using additives such as trichloroacetic acid. Accordingly, the obtained κ-casein glycomacropeptides can be used as raw materials in the fields of the food and medical supplies. It is very useful in industrial fields.

DESCRIPTION OF PREFERRED EMBODIMENTS

The following Examples illustrate the present invention more specifically.

EXAMPLE 1

Preparation of a κ-Casein Glycomacropeptide From Whey Protein Concentrate

One kg of whey protein concentrate (manufactured by Taiyo Kagaku Ltd., Trade name: Sunlact N-2) was dissolved in 50 liters of water at 50° C. and the pH value was adjusted to 3.5 by using 12N hydrochloric acid. The solution was filtered with an ultrafiltration membrane having the fraction molecular weight of 20,000 (manufactured by DDS Ltd., GR 61PP) at 50° C., at a pressure of 0.4 MPa and an average permeation flux of 52.4 l/m$^2$·h. When the filtrate volume arrived to 40 liters, 40 liters of water heated at 50° C. was added to the concentrated solution and the ultrafiltration of the concentrated solution was successively conducted. By the successive operation, the amount of the obtained filtrate was 160 liters.

To the obtained filtrate, 25% sodium hydroxide was added to obtain a solution having pH 7.0. Again, using the same ultrafiltration membrane under the same conditions, the filtrate was concentrated and 5 liters of the desalted concentrate was obtained. Then, water heated at 50° C. was added to the concentrated solution to maintain a total amount of 10 liters, the concentrated solution was treated with the same ultrafiltration membrane under the same conditions by diafiltration to desalt the concentrate. When the filtrate volume went up to 80 liters, the addition of water to the concentrated solution was stopped. When the volume of the concentrated solution was reduced to two liters by ultrafiltration, the concentration solution was freeze-dried. 54 g of the κ-casein glycomacropeptide was obtained. The purity 82% of the product was determined by an urea-SDS electrophoresis method. In the urea-SDS electrophoresis method, a sample was electrophoresed and dyed by using Coomassie brilliant blue. The peak area of the obtained dyed gel was measured with a densitometer (GELMAN ACD-12) to determined the GMP purity of the sample.

EXAMPLE 2

Preparation of a κ-Casein Glycomacropeptide From Cheese Whey

The pH value of 500 liters of Gouda cheese whey (manufactured by SNOW BRAND MILK PRODUCTS CO., LTD.) was adjusted to 3.5 by using concentrated hydrochloric acid and insolubles were removed with a clarifier. The whey solution was heated to 50° C. by using a plate heater. Using the same conditions as in Example 1, the solution was concentrated to obtain 20% of the solid content. To 360 liters of the obtained filtrate, an aqueous solution of 25% sodium hydroxide was added to obtain a solution having pH 7.0. Using the same method as in Example 1, the solution was concentrated, desalted and freeze-dried. 5.7 g of the κ-casein glycomacropeptide was obtained. The purity 80% of the product was determined by an urea-SDS electrophoresis method.

EXAMPLE 3

Preparation of a κ-Casein Glycomacropeptide From Cheese Whey Excluding Protein

The pH value of 500 liters of Gouda cheese whey (manufactured by SNOW BRAND MILK PRODUCTS CO., LTD.) was adjusted to 4.6 by using concentrated hydrochloric acid and the protein was precipitated, and then supernatant was obtained by decantation. The obtained supernatant was heated at 80° C. for 10 minutes, and insolubles were removed with a clarifier. After cooling to 50° C., the pH value of the supernatant was adjusted to 3.5 by using concentrated hydrochloric acid. Maintaining the temperature of 50° C. and using the same conditions as in Example 2, the concentrated solution was concentrated to obtain 20% of the solid content. To 410 liters of the obtained filtrate, an aqueous solution of 25% sodium hydroxide was added to obtain a solution having pH 7.0. Using the same method as in Example 1, the solution was concentrated, desalted and freeze-dried. 6.5 g of the κ-casein glycomacropeptide was obtained. The purity 78% of the product was determined by an urea-SDS electrophoresis method.

EXAMPLE 4

Preparation of a κ-Casein Glycomacropeptide From Whey Protein Concentrate and Desalting and Concentration of the Peptide With a Loose RO Membrane One kg of whey protein concentrate (manufactured by Taiyo Kagaku Company, Trade name: Sunlact N-2) was dissolved in 50 liters of water at 50° C. Using the same method as in Example 1, the solution was ultrafiltered and 160 liters of filtrate was obtained. The pH value of the filtrate was held at 3.5. The filtrate was filtered with an ultrafiltration membrane having the fraction molecular weight of 5,000 (manufactured by DDS Company, GR 81PP) at 50° C., at a pressure of 0.4 MPa and an average permeation flux of 38.8 $l/m^2 \cdot h$. When the volume of the concentrated solution was reduced to two liters by desalting and concentration, the concentrated solution was freeze-dried. 54 g of the κ-casein glycomacropeptide was obtained. The purity 80% of the product was determined by an urea-SDS electrophoresis method.

We claim:

1. A process for producing a κ-casein glycomacropeptide, comprising:
   adjusting the pH of a solution of milk starting materials containing the κ-casein glycomacropeptide to below 4;
   after said adjusting step, treating the solution by ultrafiltration with a membrane having a molecular weight cut-off of 10,000–50,000; and
   collecting the obtained filtrate which will contain the κ-casein glycomacropeptide.

2. A process as claimed in claim 1, further including the step of concentrating the obtained filtrate by readjusting the pH value of the filtrate obtained by the ultrafiltration treatment to 4 or higher and concentrating by ultrafiltration with a membrane having a molecular weight cut-off of 50,000 or less.

3. A process as claimed in claim 1, further including the step of concentrating the collected filtrate by ultrafiltration with a membrane having a molecular weight cut-off of 10,000 or less.

4. A process in accordance with claim 1, wherein said step of adjusting the pH is accomplished without trichloroacetic acid.

5. A process in accordance with claim 1, wherein the membrane used in said treating step, has a molecular weight cut-off of about 20,000.

6. A process in accordance with claim 2, wherein the membrane used in said treating step, has a molecular weight cut-off of about 20,000.

7. A process in accordance with claim 2, wherein the membrane used in said concentrating step has a molecular weight cut-off of about 20,000.

8. A process in accordance with claim 6, wherein the membrane used in said concentrating step has a molecular weight cut-off of about 20,000.

* * * * *